US009733172B2

(12) United States Patent
Kismarton

(10) Patent No.: US 9,733,172 B2
(45) Date of Patent: Aug. 15, 2017

(54) UNIVERSAL GRIP SYSTEM

(71) Applicant: The Boeing Company, Chicago, IL (US)

(72) Inventor: Max U. Kismarton, Renton, WA (US)

(73) Assignee: The Boeing Company, Chicago, IL (US)

( * ) Notice: Subject to any disclaimer, the term of this patent is extended or adjusted under 35 U.S.C. 154(b) by 443 days.

(21) Appl. No.: 14/286,926

(22) Filed: May 23, 2014

(65) Prior Publication Data

US 2015/0338325 A1 Nov. 26, 2015

(51) Int. Cl.
- *G01N 3/02* (2006.01)
- *B25B 5/00* (2006.01)
- *B25B 5/08* (2006.01)
- *B25B 5/02* (2006.01)
- *G01N 3/04* (2006.01)

(52) U.S. Cl.
CPC ............... *G01N 3/02* (2013.01); *B25B 5/003* (2013.01); *B25B 5/02* (2013.01); *B25B 5/08* (2013.01); *G01N 3/04* (2013.01); *G01N 2203/0447* (2013.01)

(58) Field of Classification Search
CPC ............. G01N 3/04; G01N 2203/0067; G01N 2203/0075; G01N 2203/0282; G01N 3/02; B25B 5/003; B25B 5/006; B25B 5/08; B25B 5/085; B25B 5/1002; B25B 5/02; B25B 5/145; B25B 5/16; B25B 5/163; B25B 5/166
USPC .......... 73/826, 855, 830, 831, 833, 788, 859
See application file for complete search history.

(56) References Cited

U.S. PATENT DOCUMENTS

| 3,715,916 A | * | 2/1973 | Stickney | .................. G01N 3/04 73/859 |
| 4,888,995 A | * | 12/1989 | Curtis | ...................... G01N 3/04 73/859 |

(Continued)

OTHER PUBLICATIONS

"MTS 810 and 858 Material Testing Systems", MTS Systems Corporation, 2006, Retrieved from the Internet: <http://www.upc.edu/pct/documents_equipament/d_77_id-412.pdf>, Accessed on Jun. 11, 2014, 28 pgs.

(Continued)

*Primary Examiner* — Lisa Caputo
*Assistant Examiner* — Philip Cotey
(74) *Attorney, Agent, or Firm* — Kwan & Olynick LLP

(57) ABSTRACT

Provided are universal grip systems and method of using universal grip systems to test coupons. According to various examples, a universal grip system includes two grips and two guide posts for supporting the two grips and allowing the two grips to move with respect to each other. Each grip may include one or two wedges. The wedges are used to engage the coupons during testing and provide anti-buckling support and/or anti-rotation support. The wedges are slidably coupled within corresponding grips, which allows the universal grip system to engage and disengage the coupons by moving one grip with respect to another. The grips may be constructed from thermally neutral materials, such as invar 36. The grips may thermally isolated from the guide posts by, for example, a set of spacers disposed between the grips and linear bearing slidably coupled to the guide posts.

19 Claims, 11 Drawing Sheets

(56) References Cited

U.S. PATENT DOCUMENTS

| | | | | |
|---|---|---|---|---|
| 4,998,825 A * | 3/1991 | Hublikar | ............... | G01N 3/18 33/787 |
| 5,054,324 A * | 10/1991 | Pohl | ............... | G01N 3/04 73/859 |
| 5,095,757 A * | 3/1992 | Larsen | ............... | G01N 3/04 73/857 |
| 5,188,456 A * | 2/1993 | Burke | ............... | G01N 3/08 374/50 |
| 5,224,386 A * | 7/1993 | Curtis | ............... | G01N 3/04 73/833 |
| 5,297,441 A * | 3/1994 | Smith | ............... | G01N 3/04 73/818 |
| 5,377,549 A * | 1/1995 | Werner | ............... | G01N 3/04 73/856 |
| 5,505,095 A * | 4/1996 | Raymond | ............... | G01N 3/04 73/831 |
| 5,512,727 A * | 4/1996 | Myers | ............... | G01N 3/04 219/201 |
| 5,528,942 A * | 6/1996 | Baratta | ............... | G01N 3/02 73/818 |
| 5,693,890 A * | 12/1997 | Holmes | ............... | G01N 3/04 73/826 |
| 5,948,994 A * | 9/1999 | Jen | ............... | G01N 3/08 73/796 |
| 2002/0166387 A1 * | 11/2002 | Grote | ............... | G01N 3/04 73/857 |
| 2004/0144180 A1 * | 7/2004 | Imamura | ............... | G01N 3/08 73/796 |
| 2006/0070452 A1 * | 4/2006 | Bohlmann | ............... | G01N 3/08 73/800 |
| 2006/0260413 A1 * | 11/2006 | Kraemer | ............... | G01N 3/04 73/818 |
| 2007/0107534 A1 * | 5/2007 | Lemmer | ............... | G01N 3/04 73/857 |
| 2007/0227259 A1 * | 10/2007 | Alba | ............... | G01N 3/16 73/831 |
| 2008/0257120 A1 * | 10/2008 | Tsai | ............... | G01N 3/04 81/418 |
| 2009/0007689 A1 * | 1/2009 | Kawano | ............... | G01N 3/32 73/788 |
| 2009/0007692 A1 * | 1/2009 | Ferguson | ............... | G01N 3/08 73/831 |
| 2009/0139343 A1 * | 6/2009 | Lindeman | ............... | G01N 3/04 73/856 |
| 2009/0139344 A1 * | 6/2009 | Lindeman | ............... | G01N 3/04 73/859 |
| 2009/0199651 A1 * | 8/2009 | Park | ............... | B25J 7/00 73/796 |
| 2011/0179877 A1 * | 7/2011 | Hanoomanjee | ............... | B25B 5/08 73/662 |
| 2012/0222491 A1 * | 9/2012 | Williams | ............... | G01N 3/04 73/856 |
| 2013/0042696 A1 * | 2/2013 | Fukuda | ............... | G01N 3/04 73/800 |
| 2014/0352451 A1 * | 12/2014 | Kismarton | ............... | G01N 3/02 73/826 |

OTHER PUBLICATIONS

Davis, Joseph R., "Tensile Testing", ASM International, 2nd Edition, 2004, Retrieved from the Internet: <http://books.google.com/books?id=5uRlb3emLY8C&pg=PA66&lpg=PA66&dq=crosshead+load+screw+material+testing&source=bl&ots=Or441ldm1J&sig=h4JitMzmZqbLpJ2UM-hsxnPwZsc&hl=en&sa=X&ei=B23yUvrEJ5KEoQS4l4GoBA&ved=0CE4Q6AEwAQ#v=onepage&q=crosshead%20load%20screw%20mat>, Accessed on Jun. 11, 2014, pp. 66-67.

* cited by examiner

UNIVERSAL GRIP SYSTEM

TECHNICAL FIELD

The present disclosure relates to a universal grip system for performing coupon level mechanical testing to test or qualify materials in a variety of environmental conditions.

BACKGROUND

Various materials may need to be qualified for usage in a variety of industries including transportation and aerospace, among others. These materials can be tested within a material test system designed to perform a variety of operations including tension, compression, and/or bearing tests. Samples of these materials, referred to herein as coupons, are typically formed into specific shapes (e.g., rectangular or round shapes) that can be placed into a material test system and tested according to various testing specifications.

In order to test a coupon using a material test system, the coupon must be guided and supported by a fixture that both holds and stabilizes the coupon during the application of loads or other forces. Various gipping fixtures are used for these purposes. Conventional gripping fixtures typically include manually assembled devices, sometimes referred to as support fixtures, between which an operator places a coupon for testing. These fixtures are manually assembled outside of the test system (and test environment) and placed in the test system in an assembled state together with a coupon.

However, existing conventional fixtures are highly inefficient. In particular, many support fixtures require manual assembly and disassembly for each coupon to be tested. For test conditions that involve specific temperature and humidity levels, materials testing may be performed within an environmental chamber. Manual assembly and disassembly of the support fixtures typically disturbs environmental conditions because every time the environmental chamber is opened and the fixtures are removed from the environmental chamber, it takes time to reestablish the test conditions. Once the fixture is placed back into the environmental chamber, the desired conditions must be reestablished before testing can be performed on a particular coupon.

Because manual assembly and disassembly of a support fixture is required for testing of each coupon, this testing usually requires the full attention of a dedicated operator. Accordingly, manual assembly and disassembly is time consuming and labor intensive. If a batch of coupons is to be tested, significant time and resources must be devoted to such testing. For example, a testing cycle may take between 30-60 minutes for a single coupon. Consequently, it is desirable to provide improved mechanisms for performing testing on coupons.

SUMMARY

Provided are universal grip systems and method of using universal grip systems to test coupons. According to various examples, a universal grip system includes two grips and two guide posts for supporting the two grips and allowing the two grips to move with respect to each other. Each grip may include one or two wedges. The wedges are used to engage the coupons during testing and provide anti-buckling support and/or anti-rotation support. The wedges are slidably coupled within corresponding grips, which allows the universal grip system to engage and disengage the coupons by moving one grip with respect to another. The grips may be constructed from thermally neutral materials, such as invar 36. The grips may thermally isolated from the guide posts by, for example, a set of spacers disposed between the grips and linear bearing slidably coupled to the guide posts.

According to various examples, a universal grip system includes a first grip and a second grip. The first grip includes a first wedge slidably supported in the first grip. In some examples, the first grip may include an additional wedge for engaging a coupon together with the first wedge. Alternatively, the first grip includes a positioning block for engaging a coupon together with the first wedge. The second grip includes a second wedge slidably supported in the second grip. In some examples, the second grip may include an additional wedge for engaging a coupon together with the second wedge. Alternatively, the sedge grip includes a positioning block for engaging a coupon together with the second wedge. The universal grip system also includes a first guide post and a second guide post. The first grip and the second grip are each slidably coupled to the first guide post and the second guide post such that the first grip and the second grip are movable with respect to each other in a first sliding direction. The first guide post and the second guide post prevent the first grip and the second grip from moving in any direction other than the first sliding direction.

In one aspect, which may include at least a portion of the subject matter of any of the preceding and/or following examples and aspects, the first wedge is movable with the first grip in a second sliding direction not parallel to the first sliding direction. As such, when the first grip moved in the first sliding direction relative to the second grip, the first wedge may slide in the second sliding direction and engage the coupon. Because the second sliding direction is not parallel to the first sliding direction, the second sliding direction includes a component perpendicular to the first sliding direction.

In one aspect, which may include at least a portion of the subject matter of any of the preceding and/or following examples and aspects, the first grip further includes a third wedge slidably supported in the first grip. The third wedge is movable with the first grip in a third sliding direction not parallel to the first sliding direction. During operating of the universal grip system, the coupon is engaged by the first wedge and the third wedge, which provide support to the coupon within the first grip.

In one aspect, which may include at least a portion of the subject matter of any of the preceding and/or following examples and aspects, the universal grip system also includes a base clip engaging the first wedge and the third wedge. The base clip allows the first wedge and the third wedge to move with respect to each other in a direction normal to the first sliding direction. The first wedge and the third wedge move in this direction with respect to each other in order to engage or disengage the coupon.

In one aspect, which may include at least a portion of the subject matter of any of the preceding and/or following examples and aspects, the universal grip system also includes a link plate. The link plate aligns the first wedge and the third wedge relative to each other within a plane parallel to the first sliding direction. As such, the link plate maintains in part the orientation of the first wedge and the third wedge within the first grip. The link plate may be removable.

In one aspect, which may include at least a portion of the subject matter of any of the preceding and/or following examples and aspects, the universal grip system also includes an actuator interface having a surface engaging the first wedge and the third wedge. The actuator interface helps to maintain the alignment of the first wedge and the third wedge within a plane normal to the first sliding direction.

In one aspect, which may include at least a portion of the subject matter of any of the preceding and/or following examples and aspects, the first grip includes a first guide block. The first guide block slidably supports the first wedge. The first grip may also include a second guide block, the second guide block slidably supporting an additional wedge (e.g., the third wedge described above) or fixedly supporting a positioning block.

In one aspect, which may include at least a portion of the subject matter of any of the preceding and/or following examples and aspects, the first grip also includes a retainer clip engaging the first guide block and first wedge. The retainer clip allows the first wedge to slide relative to the first guide block.

In one aspect, which may include at least a portion of the subject matter of any of the preceding and/or following examples and aspects, the first grip a thermally neutral material. The second grip may also include a thermally neutral material, which may be same or different than the thermally neutral material of the first grip.

In one aspect, which may include at least a portion of the subject matter of any of the preceding and/or following examples and aspects, the first grip is thermally insulated from the first guide post and second guide post. The second grip may be also thermally insulated from the first guide post and second guide post. For example, the first grip and second grip are thermally insulated from the first guide post and the second guide post by ceramic spacers. Specifically, the first grip may be slidably coupled to the first guide post using a first linear bearing. One of the ceramic spacers may be disposed between the first linear bearing and the first grip.

In one aspect, which may include at least a portion of the subject matter of any of the preceding and/or following examples and aspects, the first grip includes a grip zone for gripping a coupon during testing and a support zone for preventing buckling and rotation of the coupon during testing. The support zone has a wider spacing between the first wedge and the second wedge than the grip zone.

In one aspect, which may include at least a portion of the subject matter of any of the preceding and/or following examples and aspects, the first wedge and the second wedge are made from a material having a coefficient of thermal expansion less than $6 \times 10^{-6}$ inch/inch ° F. For example, the first wedge and the second wedge are made from invar 36.

According to various examples, a method for testing of a coupon involves securing the coupon using a universal grip system. The universal grip system includes a first grip and a second grip. The first grip includes a first wedge slidably supported in the first grip, while the second grip includes a second wedge slidably supported in the second grip. Securing the coupon may involve sliding the first wedge in the first grip and sliding the second wedge in the second grip and engaging the coupon with the first wedge and the second wedge as the first grip moves relative to the second grip. The method proceeds with transmitting a load to the coupon based on a signal from a control system. Transmitting the load may involve moving the first grip relative to from the second grip. The method also involves releasing the coupon from the universal grip system. Releasing the coupon may involve sliding the first wedge in the first grip and sliding the second wedge in the second grip and disengaging the coupon from the first wedge and the second wedge as the first grip moves relative to the second grip.

In one aspect, which may include at least a portion of the subject matter of any of the preceding and/or following examples and aspects, the first grip and the second grip are each supported by a first guide post and a second guide post as the first grip moves relative to the second grip during securing the coupon, transmitting the load, and releasing the coupon. The first grip and the second grip may be each thermally isolated from the first guide post and the second guide post.

These and other embodiments are described further below with reference to the figures.

DETAILED DESCRIPTION OF EXAMPLE EMBODIMENTS

Figure 1:
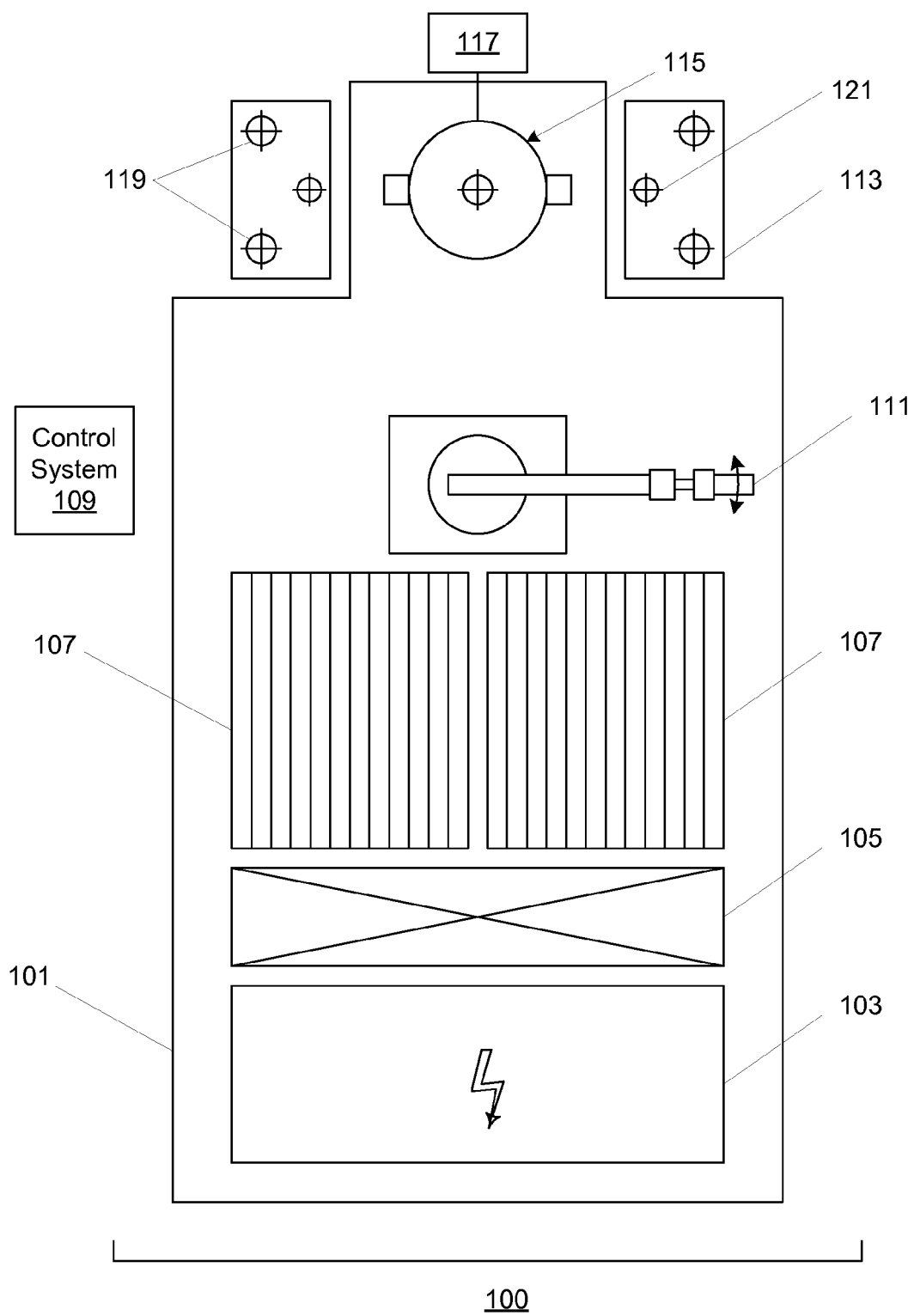
FIG. 1 is a diagrammatic representation of a material test system, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

Various materials may need to be qualified for usage in a variety of industries including transportation and aerospace, among others. Samples of these materials, referred to herein as coupons, can be tested within a materials test system designed to perform a variety of operations including tension, compression, and bearing tests. In order to test a coupon within a materials test system, the coupon must be held in place by a gripping system that both holds and stabilizes the coupon during the application of loads or other forces.

Existing gripping systems require manual assembly and disassembly of supporting fixtures within a test frame for each coupon to be tested. When environmental testing is required (e.g., 180 degrees Fahrenheit and 100% humidity), testing of one coupon can take about 30 minutes to an hour because manual assembly of the gripping system and supporting fixtures for a coupon is labor and time intensive. In addition, each time the test chamber is opened and another coupon inserted into the test machine, it can take about 15-20 minutes to re-stabilize the test conditions. Specifically, the testing process for one coupon can include: assembling a fixture (which can take around 15 minutes), installing the fixture and stabilizing the temperature in the chamber (which can additionally take around 15 minutes), testing of the coupon (which can take around 3 minutes), and retrieval and disassembly of the fixture (which can take around 15 minutes more). The net result may be a 1-2 coupons per hour throughput for materials testing in some examples, which is highly inefficient.

Furthermore, an operator must devote full attention to the testing process using conventional gripping systems because the testing is so mechanically intensive. Accordingly, it is difficult to multitask during testing. Furthermore, operator downtime is also common (e.g., breaks, distractions). Accordingly, many existing systems allow a daily throughput of only about 7 coupons per day.

According to various embodiments, the universal grip system described herein provides a mechanism for securing a coupon for testing without manual assembly of any of the supporting fixtures. In particular, the universal grip system is designed to operate in a robotic environment that allows coupons to be loaded and secured for testing automatically within an environmental test chamber. In this configuration, a tray full of coupons is placed within the chamber and the coupons can be tested sequentially without manual assembly or disassembly of the grip system or any supporting features. Because testing for all of the coupons in the tray can be done without the need to open the chamber, the conditions within the chamber can be kept stable throughout sequential testing of the coupons. According to various examples, this configuration allows the coupons to be tested at a rate of 30-60 coupons per hour. This is a 10-20 times improvement in cost and time savings over existing manual systems.

System Examples

The present disclosure describes various mechanisms and processes that provide a universal grip system that can be used with a mechanized material test system, according to various embodiments. With reference to FIG. 1, shown is one example of a mechanized material test system, in accordance with some embodiments. In the present example, material test system 100 includes an environmental chamber 101 that can provide temperature and humidity conditions that may be desirable for a particular test. For instance, environmental chamber 101 can provide environments with temperatures ranging from about a −73 degrees Celsius to 205 degrees Celsius (−100 degrees Fahrenheit to 400 degrees Fahrenheit) and 10% to 95% humidity between 10 degrees Celsius to 85 degrees Celsius (50 degrees Fahrenheit to 185 degrees Fahrenheit) in some examples. The environmental chamber 101 can house coupon trays 107, robot arm 111, and universal grip system 115, according to various embodiments.

In the present embodiment, environmental chamber 101 can be heated and cooled in a number of ways. In particular, heating and cooling system 103 can be used to provide the proper temperature to environmental chamber 101. Additional heating and cooling implements can include heater blankets, cal-rods (tubular heaters), and liquid nitrogen (for cooling). Heat can be transferred from heating and cooling system 103 through heat exchanger 105. In some examples, insulation tabs can be included at major junctions to prevent heat loss. These insulation tabs can provide shims for the parts, thereby allowing fine tuning of the alignment and positioning of parts relative to each other. These insulation tabs can also reduce heat flux by around 100 times.

According to various embodiments, coupons to be tested are stored in coupon trays 107. The coupons can be sized according to test specifications, and in some cases the coupons can be about 3 inches by 5 inches in size. The coupon trays can be made from bent sheet metal with two combs that are used to organize and separate the coupons from each other, according to various examples. In some instances, a coupon tray can be removed or inserted through a drawer in the side of the environmental chamber, which can reduce the amount of disturbance to the environmental conditions within the chamber even when the trays are moved or replaced.

In particular embodiments, robot arm 111 can automatically move a coupon to be tested from a coupon tray 107 to universal grip system 115. This robot arm 111 can operate within the environmental chamber based on commands from a control system 109, according to various examples. In particular, the robot arm can locate a coupon to be tested, pick up the coupon, move the coupon to the universal grip system, and release the coupon to the universal grip system 115. The robot arm 111 can repeat this process for sequential testing of coupons without the need to open or otherwise disturb the environmental chamber 101 between tests.

In the present embodiment, universal grip system 115 can be located within environmental chamber 101 and positioned within a materials test frame 113. The universal grip system 115 can hold a coupon during such tests as compression, bearing, and tension. In addition, the universal grip system 115 can automatically receive a coupon from robot arm 111 and can position and secure the coupon during an application of forces by materials test frame 113. The universal grip system 115 can then release the tested coupon, which may then pass to a disposal system in some examples. The universal grip system 115 can then receive additional coupons for testing in a sequential manner within environmental chamber 101. In some examples, control system 109 can provide signals to universal grip system 115 that allow the universal grip system to coordinate with robot arm 111 such that the universal grip system can receive a particular coupon securely. The control system 109 can also provide signals that control actuators that move components of the universal grip system that are designed to secure the coupon for testing.

According to various embodiments, the materials test frame 113 can be a standard test frame, such as a 100 kip test frame. In some examples, this materials test frame is a crosshead test frame with crosshead guide posts 119 and crosshead load screw 121, which are located outside the environmental chamber 101. In addition, an extensometer 117 can be attached to the universal grip system 115 such that it can measure strain, displacement, etc. of a coupon during testing. This extensometer can be located outside the environmental chamber in various examples.

In some embodiments, the time it takes to complete one cycle (i.e. testing of one coupon from selection in the coupon tray 107 to disposal of the coupon from the system) in the material test system 100 shown can be in the range of about 3-5 minutes, assuming a one minute test for each coupon. Accordingly this system is capable of providing significant time and cost savings over manually loaded test systems. For example, 100 coupons can be loaded into the environmental chamber 101. The robotic system tests one coupon every three minutes, yielding a rate of 20 coupons tested per hour, in this example. As the robot continues to feed coupons to the universal grip system 115, an operator can reload the coupon trays with minimal disturbance to environmental chamber 101. This can lead to a daily throughput of around 7 trays, or 140 coupons tested per day. Accordingly, this is a significant improvement over the yield for manually loaded systems, which can typically yield only about 7 coupons tested per day. In addition, testing with this system can be performed even when unattended by an operator, which provides additional efficiencies.

Figure 2:
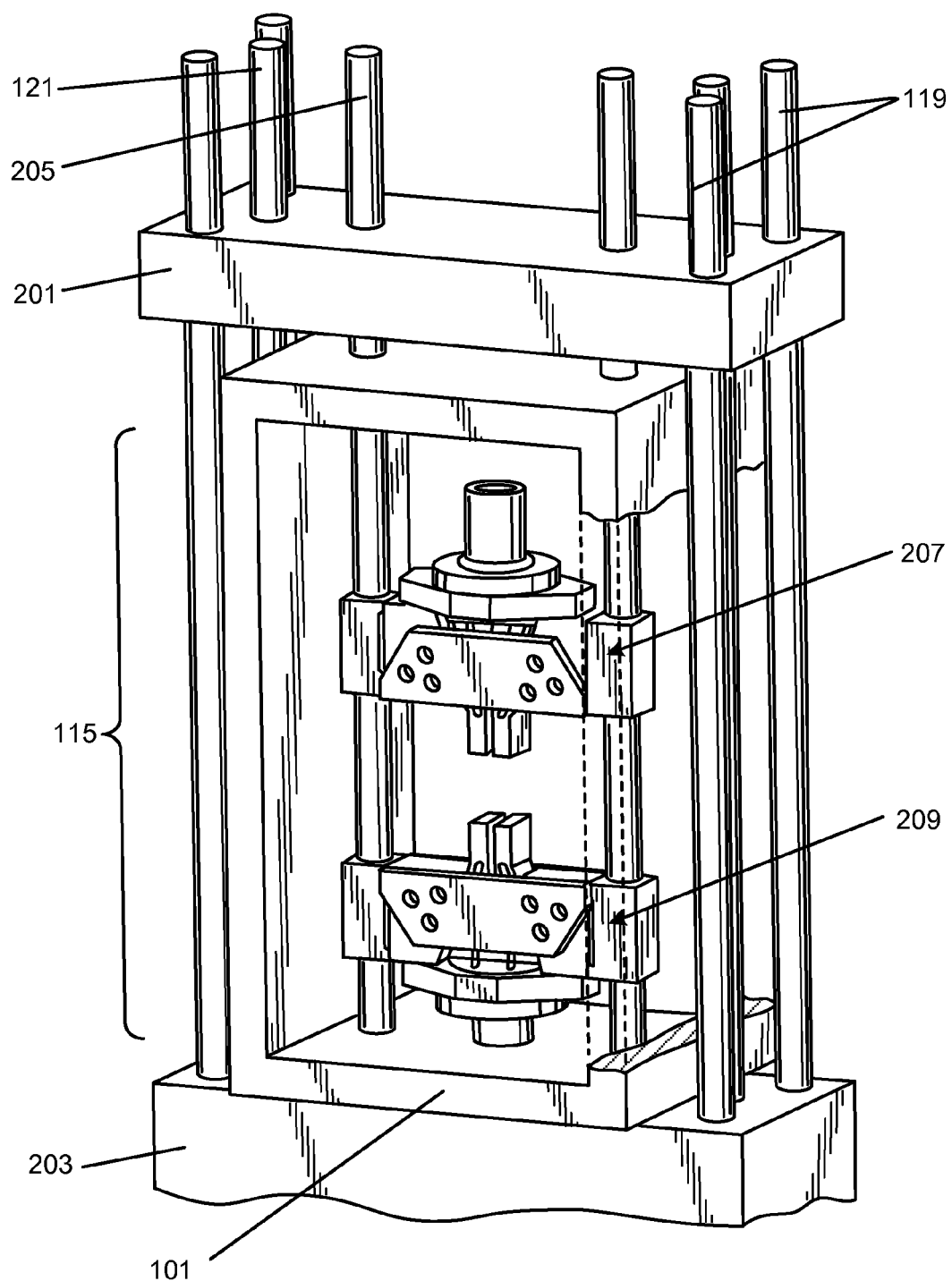
FIG. 2 is a diagrammatic representation of a materials test frame with a universal grip system installed, in accordance with some embodiments.

With reference to FIG. 2, shown is a diagrammatic representation of a material test frame with a universal grip system installed, in accordance with some embodiments. In particular, a crosshead materials test frame, such as a standard 100 kip test frame, is shown with crosshead 201, crosshead guide posts 119, crosshead load screw 121, and test frame base 203. The test frame can be in the range of about 8 feet tall in some embodiments. Environmental chamber 101 is located within the materials test frame, with the crosshead 201, guide posts 119, and load screw 121 located outside of the environmental chamber 101. Universal grip system 115 is located within the environmental chamber, and includes an upper grip assembly 207, a lower grip assembly 209, and guide posts 205. In some examples, the upper grip assembly 207 and lower grip assembly 209 can be similar to each other, such that the upper grip assembly 207 and lower grip assembly 209 include the same or substantially the same components. Accordingly, in some of the following examples and figures only the lower grip assembly 209 is described for simplicity.

In the present embodiment, the universal grip system 115 is designed to handle tension, compression, and bearing tests without extensive assembly and disassembly efforts between coupons tested. Specifically, the universal grip system 115 can be designed to handle loads of up to 100 kips in some embodiments. In some examples, coupons can be sequentially tested within the environmental chamber 101. After a certain number of coupons have been tested (such as about 100 coupons) or a different test is to be performed, the grips within universal grip system 115 can be reconfigured. In some examples, the grips must be manually configured at this point, which can take around 0.5 to 1.0 hours. About the same amount of time can also be spent on cleanup of the system during these updates.

Figure 3:
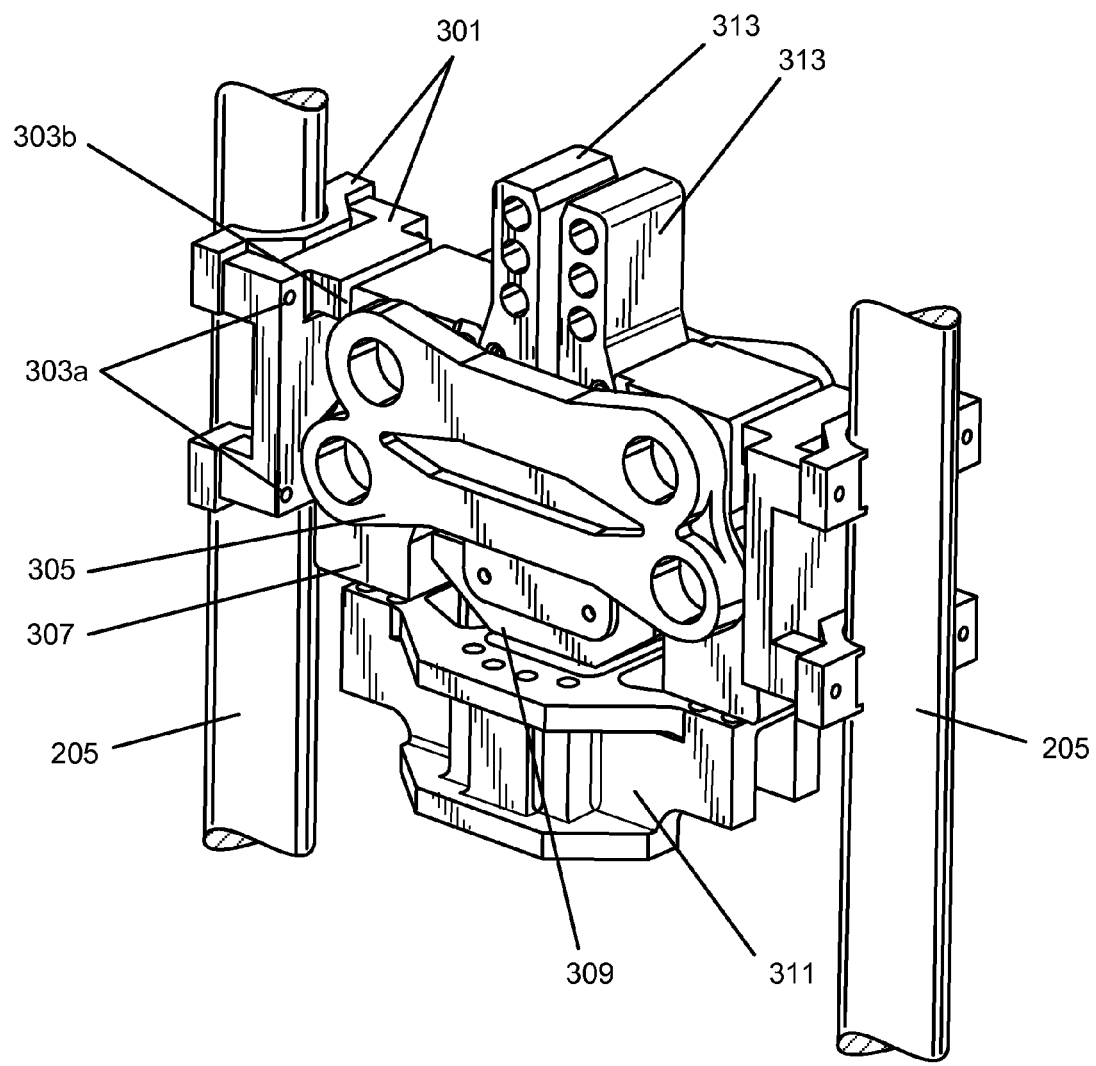
FIG. 3 is a diagrammatic representation of a lower grip assembly, in accordance with some embodiments.

With reference to FIG. 3, shown is a diagrammatic representation of a lower grip assembly, in accordance with some embodiments. As described above with regard to FIG. 2, the upper grip assembly can include many or all of the same components as the lower grip assembly in many examples, so a description of only the lower grip assembly is included here for clarity. In the present embodiment, the lower grip assembly is shown assembled between guide posts 205. These guide posts 205 can be dedicated to the grip assemblies of the universal grip system, in various examples. The lower grip assembly includes wedges 313, link plate 305, guide blocks 307, linear bearings 301, bolts 303a and 303b, test frame adapter 311, and actuator interface 309.

According to various embodiments, wedges 313 are designed to hold and secure a coupon during materials testing or, more generally, to engage the coupon during testing. As described more fully below with regard to FIG. 5, the wedges 313 can move with respect to each other, such that the wedges can grip a coupon, hold the coupon during testing, and release the coupon after testing is complete. Wedges 313 can also provide support to the coupon during various test conditions in some examples, as described in more detail below with regard to FIG. 6. In addition, wedges can take on various configurations and dimensions, depending on the application and the particular coupons and tests to be performed.

In the present embodiment, guide blocks 307 are located adjacent to the wedges 313 and are secured to each other by link plate 305. In particular, the guide blocks are secured in a fixed position relative to each other via the link plate 305, such that they remain a fixed distance apart from each other during a particular test setup. As shown in the current example, link plates can be secured on both the front and back sides of the guide blocks, such that wedges placed between guide blocks 307 are confined between guide blocks 307 and link plates 305. Although wedges 313 are confined, they can slidably contact guide blocks 307 and link plates 305, such that wedges 313 can move up and down relative to the guide blocks 307. Specifically, wedges 313 are slidably coupled guide blocks 307 such that wedges 313 can slide with respect to guide blocks 307. The sliding directions 407a and 407b are determined by orientation of contact surfaces of guide blocks 307 and wedges 313. The sliding directions 407a and 407b of wedges 313 with the grip assembly are each not parallel to the sliding direction 409 of the grip assembly within the universal grip system. Specifically, the sliding direction 409 of the grip assembly within the universal grip system may be determined by guide posts 205 and may be parallel to the center axes 411a and 411b of guide posts 205. The sliding direction wedges 313 with the grip assembly may cause wedges 313 to move closer or further away from guide posts 205 thereby engaging and/or disengaging the coupon.

According to various embodiments, link plates 305 are designed to carry opposing loads produced between the wedges 313. For instance, a 100 kip tension load applied to the coupon can result in about a 300 kip opposing load between the grip wedges. Furthermore, link plates 305 provide rigidity and stiffness to the grip assembly and a structural, removable connection between guide blocks 307. In addition, link plates 305 are designed to not grow or shrink appreciably as the temperature in the chamber varies from temperatures such as −65 degrees Fahrenheit to 400 degrees Fahrenheit. In particular embodiments, link plates 305, along with other universal grip system components, can be made using invar alloy to manage thermal growth. For example, invar or, more specifically, invar 36 may be used. The size of the link plates can be chosen for strength and stretch in some examples. For instance, the link plates can have about a 40 ksi yield, 0.010 inch elongation, about 1.5 inches in thickness, and can weigh about 45 pounds in some embodiments.

In the present embodiment, link plate 305 can be removed each time the grips are changed and/or the wedge inserts are changed. For instance, the wedge inserts may be changed to test another type of coupon or perform a different type of test. In some embodiments, wedge inserts can be changed manually after about 100 tests. At this point, the universal grip system can be cleaned and any debris from the previous tests can be removed. Once the universal grip system is cleaned out, another set of wedges can be installed and link plate 305 can be reinstalled.

According to various embodiments, guide blocks 307 can be coupled to linear bearings 301 with semi-permanent bolts at 303b. Linear bearings 301 are designed to slide along guide posts 205 in direction 409 without introducing significant friction errors. In some examples, a compensation table can be used to compensate for any friction encountered. In addition, linear bearings 301 are designed to take the loads distributed to them by the other components of the universal grip system during the application of loads to a coupon. Furthermore, because the grips must achieve and maintain chamber temperature so that the coupon maintains a desired temperature, the linear bearings are designed to limit heat transfer away from grips. Because too much heat transfer from the grips into the guide posts 205 can result in too much temperature change to the coupon, the linear bearings can be made of an insulating material. In some examples, titanium can be used as an insulating material. In addition, an air gap and/or a ceramic gasket can be used to minimize heat transfer at the interface between the linear bearings and the guide blocks 307. In particular embodiments, linear bearings 301 can be assembled with easily removable bolts at 303a, which allow servicing of the bearing material, which can include brass/Teflon in some examples.

According to various embodiments, guide posts 205 keep the universal grip system stable and prevent the components from buckling. In particular, guide posts 205 are designed to maintain precise alignment during compression testing in order to prevent misalignment (i.e., un-even stress distribution) and buckling (i.e., premature failure). In addition, guide posts 205 are designed to support sideways loading during bearing tests, and support transient loads during coupon failures, all without sustaining permanent damage to the guide posts 205. Furthermore, guide posts are designed to introduce less than about 1% error during specimen load measurements. This error can be corrected using a compensation table in some embodiments. The compensation table can be built by comparing 2 load cells: a standard test frame load cell, and a calibration unit held between grips. Both load cells can be loaded up and down along a load range, and corresponding compensation values can be recorded, which can be used to correct/adjust the readings.

In some embodiments, guide posts 205 are anchored outside of the environmental chamber. Guide posts 205 may be thermally insulated from the grip assemblies or, simply, the grips disposed within the environmental chamber. For example, ceramic spacers may be used for this thermal isolation. The ceramic spacers may be disposed between linear bearings 301 and the grip or, more specifically, between linear bearings 301 and guide blocks 307. Furthermore, the grips inside of the chamber can be made of thermally neutral material, such as invar (a nickel-iron alloy), which has a very low coefficient of thermal expansion, especially compared to ordinary steels. By constructing various components of the universal grip system from a thermally neutral material, expansion of the components due to heating is reduced. This provides less stress on the guide rods 205. Accordingly, by reducing this stress, bending and/or binding of the guide posts is reduced or prevented.

According to various embodiments, numerous components of the universal grip system can be made of invar or other material with a low coefficient of thermal expansion to avoid expansion of the components and resulting stresses that may occur with such expansion. For example, if the grip system is 30 inches wide, and the change in temperature is about 350 degrees Fahrenheit, the width of the grips would increase by about 0.065 inches if regular steel were used for the components. This would cause the linear bearings to bind on the guide posts and/or bend them, causing friction and possibly permanent damage. In some embodiments, the temperature in the chamber can vary from −65 degrees Fahrenheit to 400 degrees Fahrenheit. Accordingly, various components of the universal grip system that are located within the environmental chamber can be made from invar 36 or other material with a low coefficient of thermal expansion, in some examples.

Figure 4:
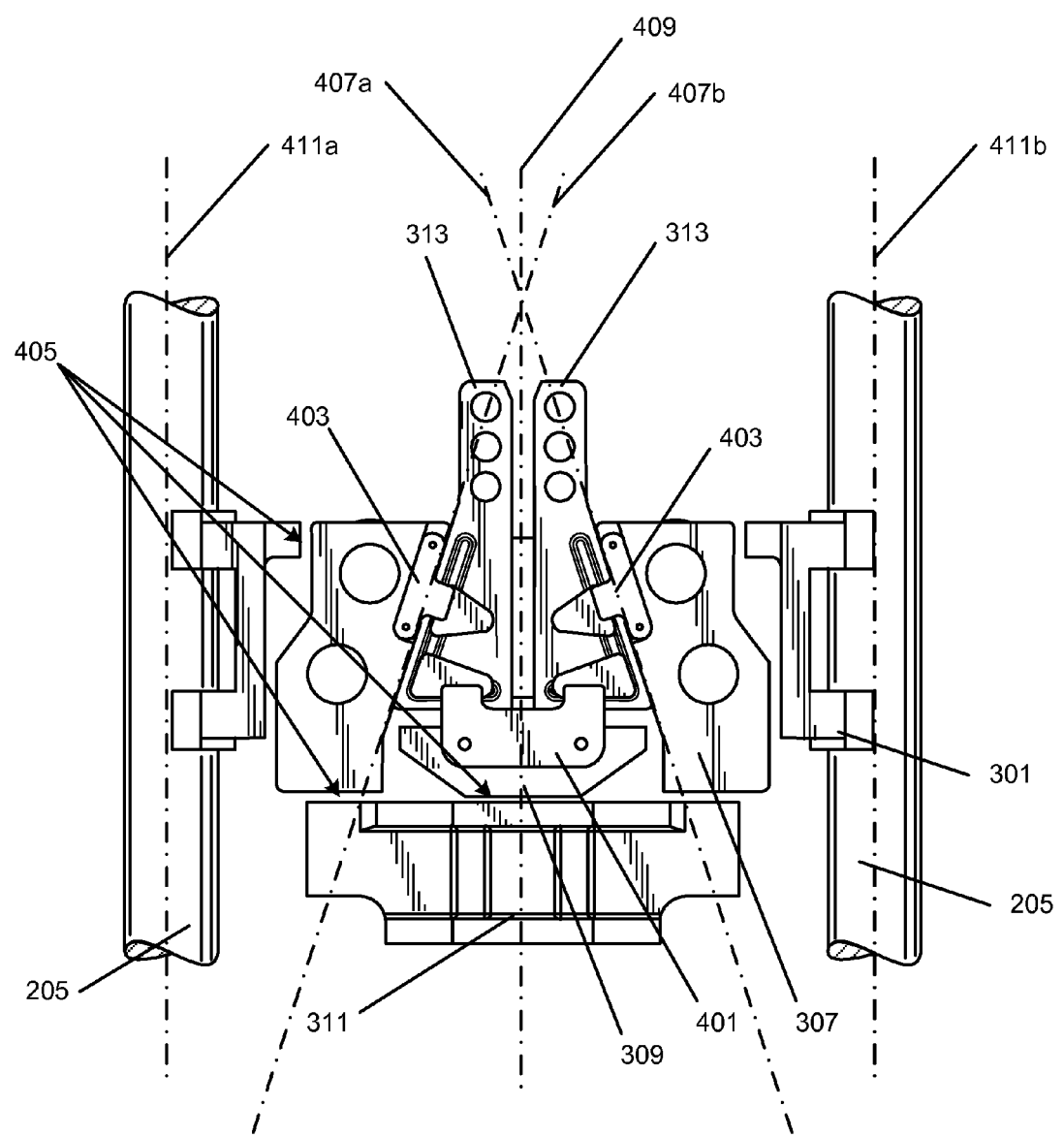
FIG. 4 is a diagrammatic representation of a portion of a lower grip assembly, in accordance with some embodiments.

With reference to FIG. 4, shown is an example of a portion of a lower grip assembly. In particular, the lower grip assembly is shown with the link plate (as shown in FIG. 3) removed. As described above with regard to FIG. 3, wedges 313 are supported by guide blocks 307. These guide blocks 307 are attached to linear bearings 301, which slide along guide posts 205, thereby allowing the universal grip assembly to move up and down during a materials test. The guide posts 205 are dedicated to supporting the upper and lower grip assemblies within the universal grip system, according to various examples. The guide posts 205 can prevent misalignment and/or buckling of the system during testing, according to various examples. In particular, the guide posts 205 can provide structural stability to the universal grip system and lateral support to the upper and lower grip assemblies during testing.

In the present embodiment, guide blocks 307 include retainer clips 403. The retainer clips 403 can fit into slots located on wedges 313, such that wedges 313 can be installed by hanging them on the retainer clips 403 before the link plate is installed. Furthermore, the retainer clips 403 can slide along slots in wedges 313 when the wedges slide up and down relative to the guide blocks 307. In addition, base clip 401 can be attached to a base such as an actuator interface 309. As shown in the present example, the base clip 401 can engage slots included in wedges 313, such that the wedges can slide laterally when engaged with the base clip, but are guided to move up and down with the actuator interface 309. The actuator interface 309 can be connected to an actuator rod (as described below with regard to FIG. 5 below) in some embodiments, and can be the actuator rod itself in other embodiments.

According to various embodiments, the universal grip system can include a test frame adapter 311, which can be designed to provide an interface between the universal grip system and the materials test frame. In some embodiments, the test frame adapter 311 can contact the base of guide blocks 307 and actuator interface 309, and provide support for these structures during testing. Furthermore, fasteners, such as bolts, can be used to connect the guide blocks 307 to the test frame adapter 311 in some examples.

In the present embodiment, thermal shims 405 (not shown in the figure, but locations of which are indicated) can be used to insulate the grip assembly such that heat flow loss is minimized. These thermal shims can be made from an insulating material such as fiberglass, ceramic, or the like, according to various examples. In some embodiments, these shims can be ½ inch fiberglass shims. In some examples, these shims can be ceramic spacers. These shims can help to concentrate the desired temperature in the coupon and grips. Otherwise, if heat were to constantly be lost from the grips to other components of the system, it would be difficult for the grips to come to or maintain a desired temperature. In addition, the shims can also be used to fine tune (e.g. +/−0.005 inch) the alignment between the grips and guide posts 205.

In some embodiments, active heating of the system can be used, which includes actively heated pads. In particular, electric heating pads can be used to more efficiently heat the samples than providing ambient heating transmitted through the air. Although not shown, these pads can be used to heat the grips and the coupon being tested in some examples.

Figure 5:
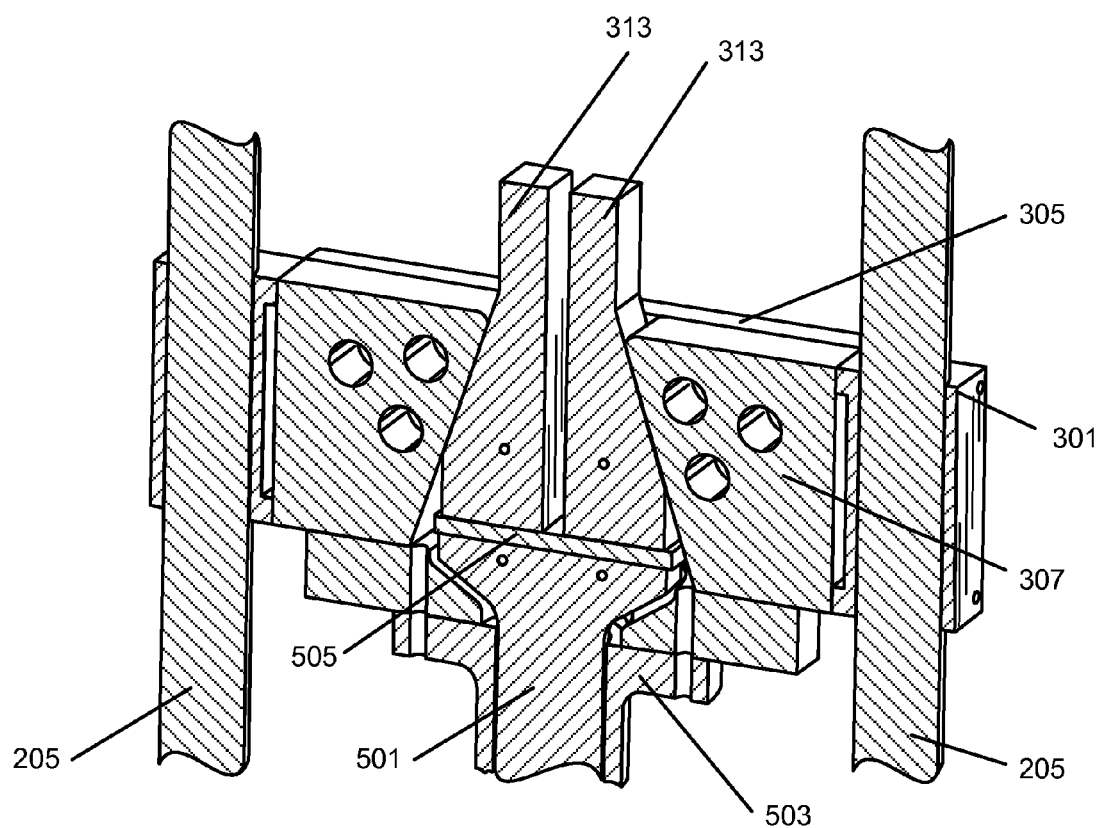
FIG. 5 is a cross-sectional view of a lower grip assembly, in accordance with some embodiments.

As described above, the wedges are designed to move with respect to the guide blocks in order to grip a coupon. With reference to FIG. 5, shown is a cross-sectional view of a lower grip assembly, in accordance with some embodiments. In particular, shown is a cross-sectional view of wedges 313, guide blocks 307, linear bearings 301, and guide posts 205. In addition, the back link plate 305 is shown secured to the guide blocks 307. In the present embodiment, actuator rod 501 contacts an optional wear plate 505 located below the wedges 313. The wear plate 505 can protect both the actuator rod 501 and the wedges 313 from surface damage due to sliding across each other.

According to the present embodiment, the actuator rod 501 and actuator sleeve 503, collectively referred to as the actuator assembly, are designed to open and close the wedges 313 such that the wedges can grip the coupon and transmit the mechanical loads applied to the coupon during a materials test. In particular, the actuator rod 501 is designed to slide up and down within actuator sleeve 503, and push the wedges 313 up and down relative to the guide blocks 307. For instance, if the actuator rod 501 pushes upward against the wedges, the wedges will slide against the inner inclined edges of the guide blocks 307. As the wedges slide upwards, they are guided towards each other by the guide blocks 307. At some point, the wedges will contact each other along an interface between them. Accordingly, when a coupon is placed between the wedges 313, the wedges will "grip" the coupon when the wedges are pushed up through the guide blocks 307. Once the coupon is secured between the wedges, the guide blocks provide support for the wedges when loads are applied to the coupon. In addition, the wedges can release the coupon when the actuator rod 501 moves down the actuator sleeve 503, as the wedges move down and apart from each other.

According to various embodiments, the movement of actuator rod 501 can be controlled by various mechanisms. In one example, a control system, such as a computer, can provide signals and commands that control the movement of the actuator rod 501. For instance, a control system can signal when a coupon will be placed between the wedges 313 and correspondingly command the actuator rod to move up a certain distance to receive and secure the coupon. The actuator rod 501 can also be used to apply the load forces to the coupon in some embodiments, and the control system can specify the loads and load patterns to be applied to the coupon. For example, the actuator rod 501 can continue an upward motion to apply compression forces to a coupon during a compression test. When a test is complete, the control system can then provide commands for the actuator rod 501 to move downwards and release the coupon from the grip system.

In the present embodiment, the actuator rod 501 and actuator sleeve 503 can be a hydraulic actuator, which is a standard component in many standard test frames. In some examples, the actuator rod 501 and actuator sleeve 503 can be part of the grip assembly. In addition, the actuator rod 501 can contact the wedges 313 directly, through a wear plate 505, or through an actuator interface 309 (as shown in FIG. 4), according to various examples. In some embodiments, actuator hydraulic components can be located outside of the environmental chamber, so that these components are not exposed to the fluctuating temperatures of the chamber that can range from about −65 degrees Fahrenheit to 400 degrees Fahrenheit. In some examples, this range can be even greater. By placing the hydraulic components outside of the chamber, durability of these components related to durability of seals, oil viscosity, etc. can be maintained without additional design requirements related to temperature fluctuations.

Figure 6:
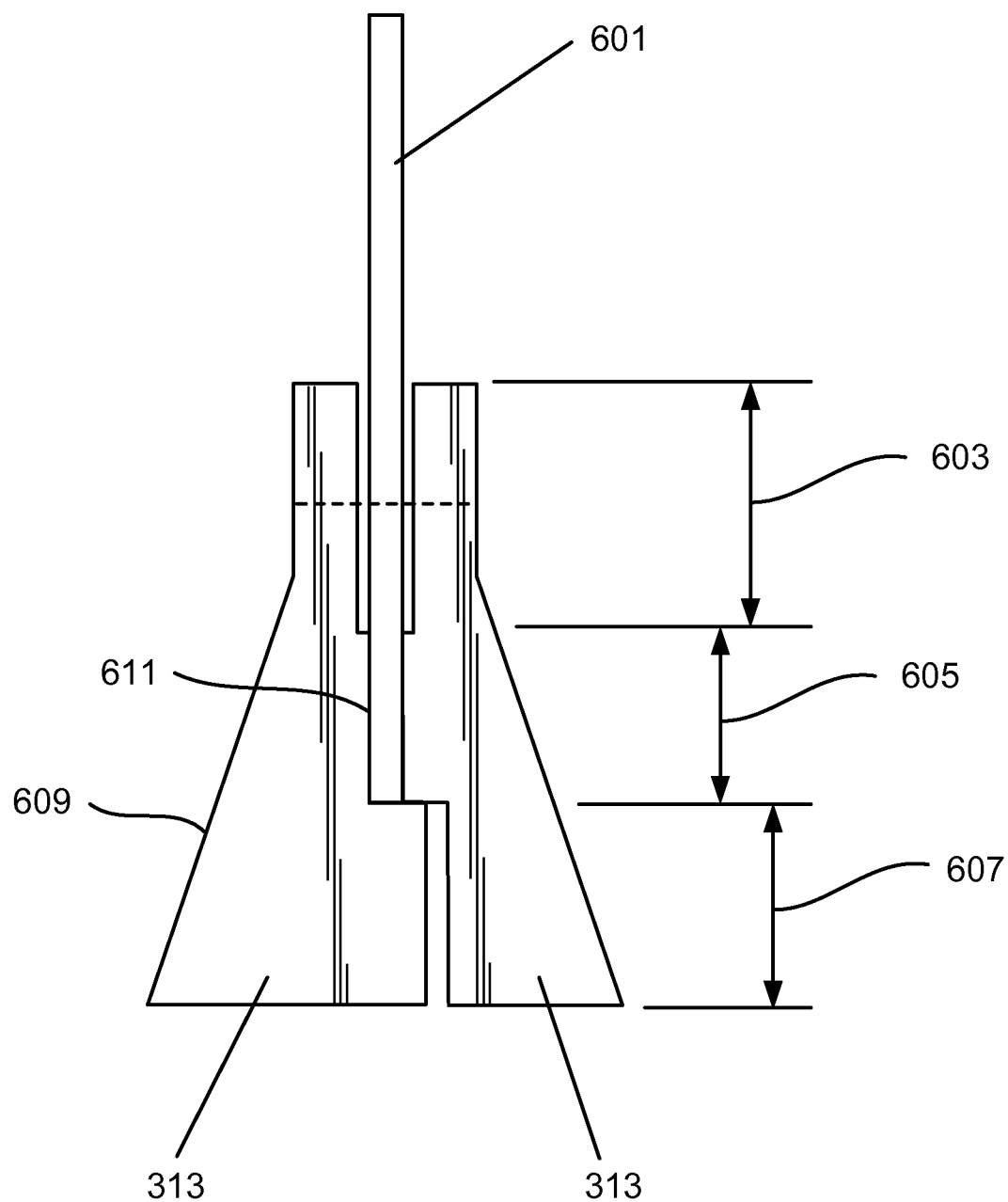
FIG. 6 is a diagrammatic representation of a wedge assembly, in accordance with some embodiments.

With reference to FIG. 6, shown is a diagrammatic representation of a wedge assembly, in accordance with some embodiments. As described above, wedges 313 can be used to secure a coupon within the universal grip system during materials testing. In the present embodiment, the wedge assembly includes two wedges 313. The wedges 313 are designed to transmit tension and/or compression loads to a coupon to be tested. In particular, the wedges can support shear loading through the face of the gripped portion of the coupon, and the wedges can support end loading applied through the cut ends of the coupons during compression. As shown in the present example, the wedges 313 can contact the coupon 601 along a grip interface 611 of the wedges and securely hold and position the coupon 601 in this region, also referred to as the grip zone 605. An interlocking notch 607 allows the two sides of the wedge assembly to interlock and act as a unit when forces are applied to the wedges. In addition, angled interface 609 of the wedges can be designed to provide support to resist heavy side loads caused by bearing and compression tests. The angled interface 609 can also be designed to slide along guide blocks 307 as described in FIGS. 3-5 above.

In the present embodiment, the wedge assembly includes an integrated support fixture that provides support from buckling and rotation of a coupon during testing. In particular, the support fixture features a support region 603 that includes an extension of the wedge that surrounds the coupon and can support a coupon laterally during compression loading to prevent buckling of the coupon. According to various embodiments, the support region 603 provides an anti-buckling support. Furthermore, the support region 603 may provide an anti-rotation support that can also laterally support coupons during bearing tests to prevent rotation of the bolted joint or joints, in various examples.

According to various embodiments, a myriad of test procedures and size combinations may be required for testing a range of materials. In order to accommodate these various test procedures and size combinations, the universal grip assembly can use multiple wedge designs that are customized for each test type and size combination. For instance, for some universal grip systems, there may be in the range of about 20-40 sets of wedges to accommodate the various test procedures and size combinations, although any number of wedges can be used depending on the application.

In the present embodiment, wedge inserts are expected to change from test to test. In some examples, the wedges 313 can be cleaned and/or changed after every 100 coupons tested. In addition, the wedges can be designed to be durable so that they will not break or wear down during testing. Furthermore, the wedges can be designed so that deflection of these pieces is minimal or reduced during the application of loads. According to various embodiments, the wedges 313 can be designed to weigh less than about 50 lbs, so they can be handled without much equipment. Although many wedges can weigh less than 25 pounds, larger wedges may be useful for large bearing and/or compression tests.

Figure 7:
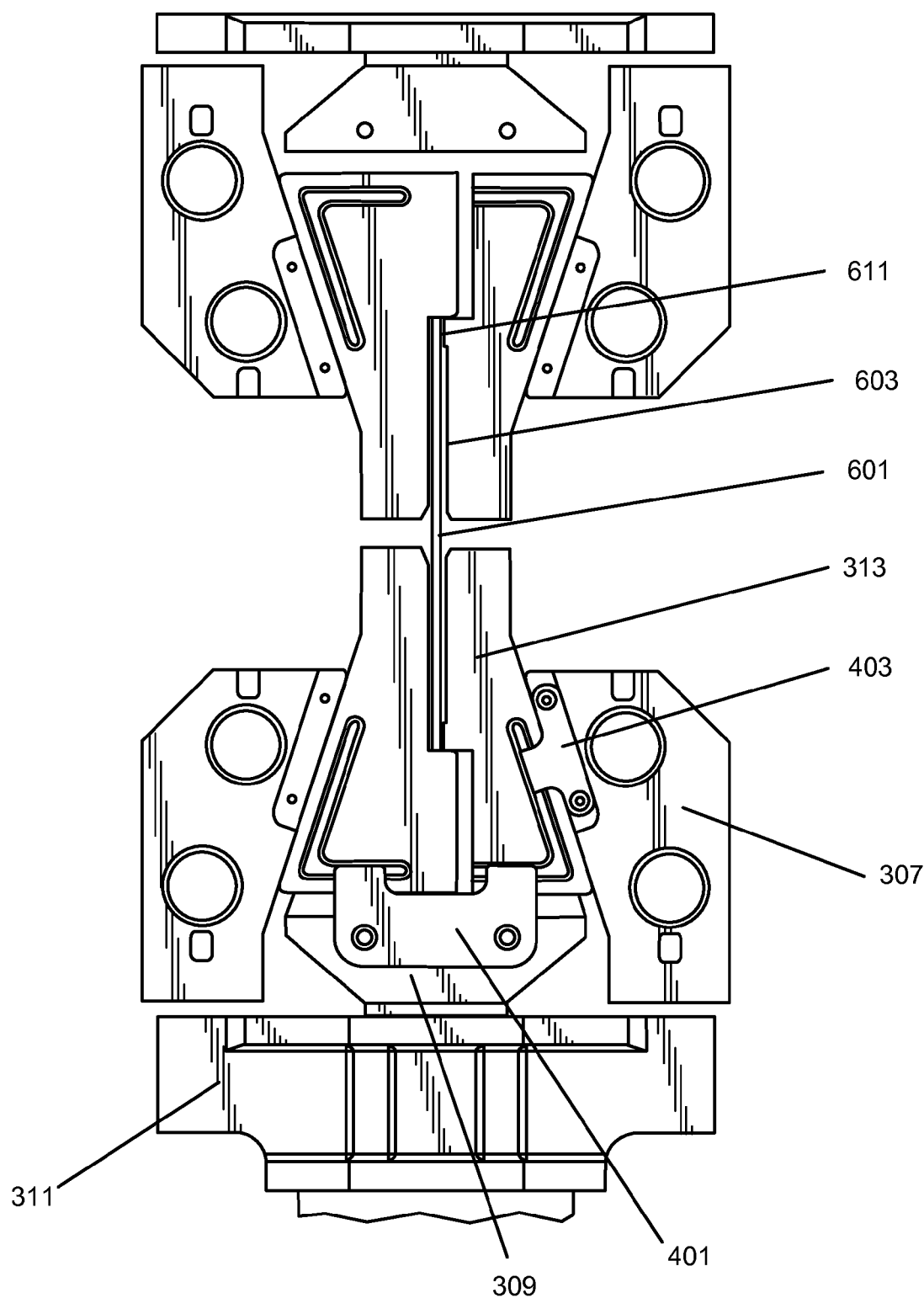
FIG. 7 is a diagrammatic representation of a universal grip system holding a coupon, in accordance with some embodiments.
Figure 8:
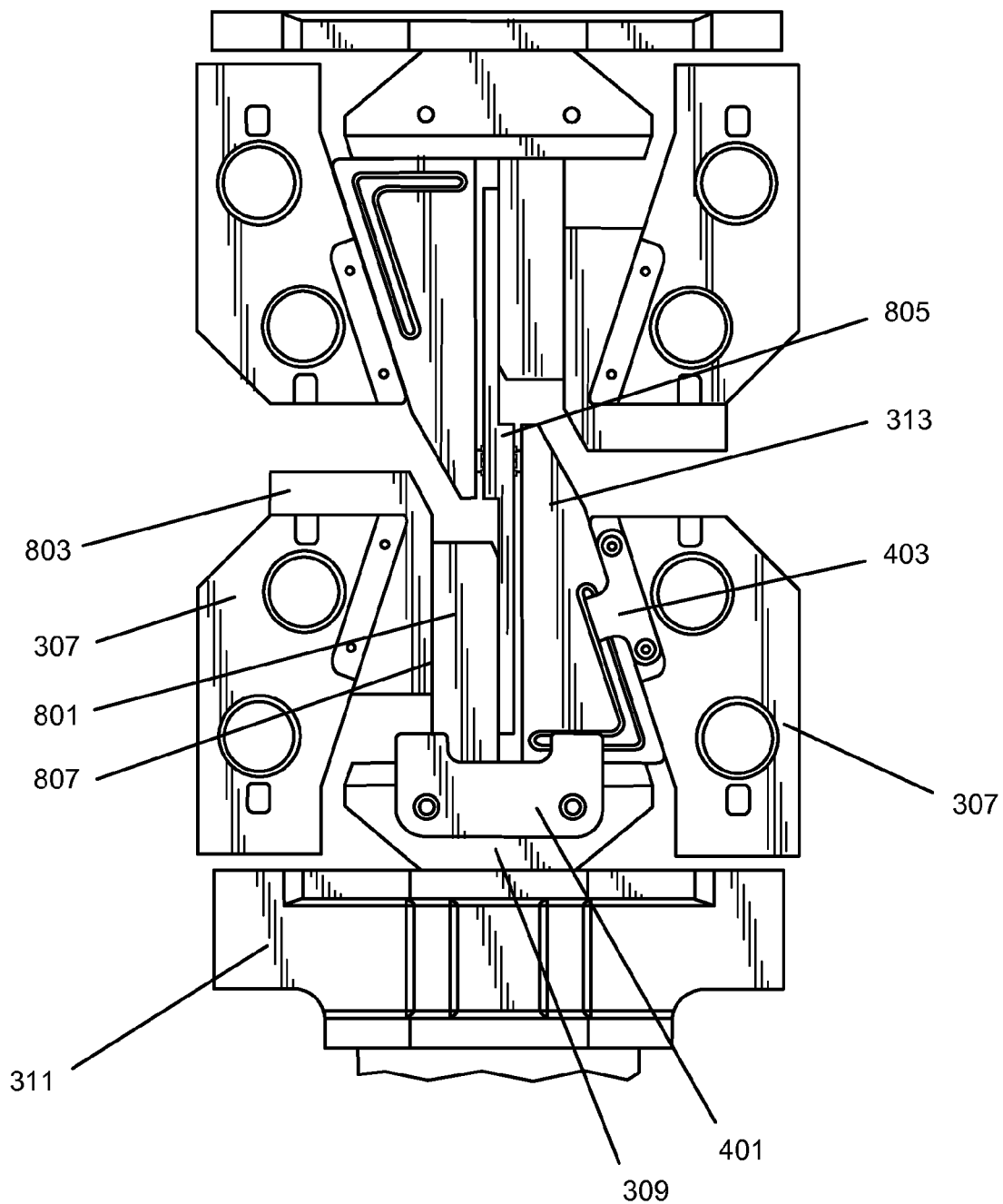
FIG. 8 is a diagrammatic representation of a universal grip system holding a coupon with a one-fastener configuration, in accordance with some embodiments.
Figure 9:
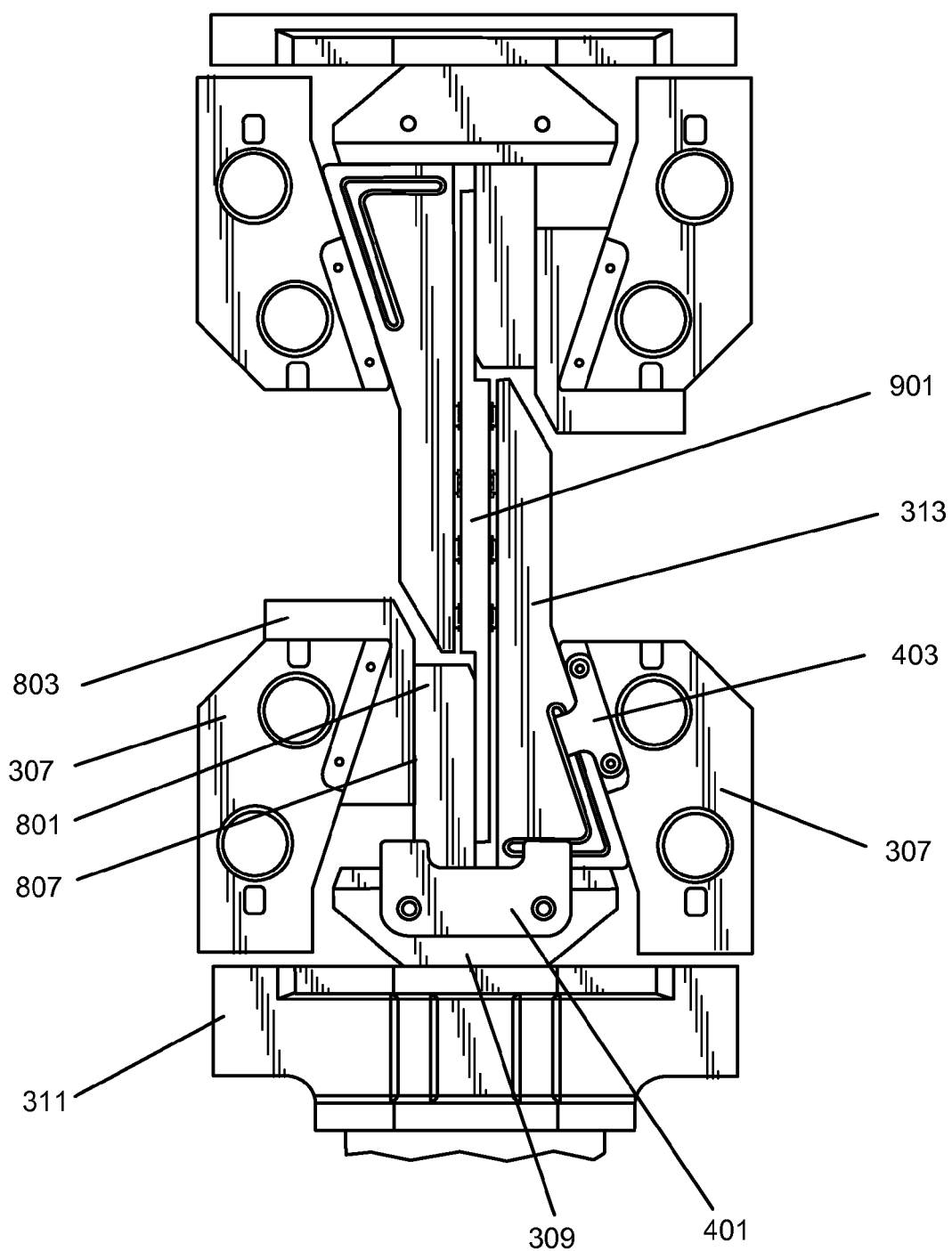
FIG. 9 is a diagrammatic representation of a universal grip system holding a coupon with a four-fastener configuration, in accordance with some embodiments.

Various wedges can be used depending on the tests to be performed and the size of the coupons to be tested. For instance, some compression tests are designed to test rectangular coupons that are uniform in composition. Other compression testscan be designed to test coupons that include fasteners or joined materials. FIGS. 7-9 show a few examples of grip systems that can accommodate different testing conditions and types of coupons. It should be recognized that these examples are merely illustrative of a few types of different configurations and various other configurations of grips, wedges, and other components can be constructed as part of the universal grip system.

With reference to FIG. 7, shown is one example of a universal grip system holding a coupon. In the present embodiment, the grip system is shown without linear bearings, guide posts, or link plates. However, both the upper and lower grips are shown holding a coupon 601. In particular, wedges 313 are shown gripping coupon 601 along the grip interface 611 and supporting the coupon with the support region 603 along the buckling restraint zone in the event of premature failure due to buckling during a compression test.

In the present embodiment, the wedges 313 are slidably attached to the guide blocks 307 with retainer clips 403, as described in more detail above with regard to FIG. 4. In addition, wedges 313 are slidably attached to actuator interface 309 via base clip 401. The guide blocks 307 can be attached to test frame adapter 311 in some examples. As shown, the wedges 313 have been pushed upwards by an actuator rod such that the wedges have closed together around the coupon 601 along the grip interface. The upper and lower grip assemblies have also been moved vertically along the guide rods (not shown) such that both the upper and lower grip assemblies have secured opposite ends of the coupon for testing. Although one particular wedge assembly and grip assembly is shown in the present embodiment, various configurations of wedges, with different dimensions and features can be included based on factors such as the type and size of the coupons to be tested and the type of testing to be performed.

With reference to FIG. 8, shown is one example of a universal grip system holding a coupon with a one-fastener configuration. In the present embodiment, the grip system is shown without linear bearings, guide posts, or link plates. However, both the upper and lower grips are shown holding a coupon 805. The coupon 805 includes one fastener joining two different samples. These samples can be made of the same or different materials, depending on the test.

In the present embodiment, the upper wedge assembly and lower wedge assembly are mirror images of one another, so only the lower wedge assembly will be described for simplicity. As shown, the lower wedge assembly includes wedge 313, first positioning block 801, and second positioning block 803. The first positioning block 801 contacts and secures the coupon along a grip interface 807 and slides vertically along an axis parallel to the coupon relative to second positioning block 803 as first positioning block 801 moves in conjunction with actuator interface 309 and wedge 313. The second positioning block 803 can be fastened to adjacent guide block 307 and can allow first positioning block 801 to slide up and down vertically against it, while providing lateral support during an application of forces during a materials test. Wedge 313 can contact coupon 805 at the location of the fastener and provide anti-rotation support at this location.

According to various embodiments, the first positioning block 801 can provide lateral support for the coupon 805 along the grip interface 807. Furthermore, the surface of wedge 313 facing coupon 805 can provide a support fixture to support the coupon 805 in the event of premature failure due to buckling during a compression test. In the present example, wedge 313 does not include a grip interface at its base, although a grip interface can be included in some embodiments. The configuration shown in the present example can be used for bearing tests according to various embodiments. For example, during some tests, bearing side loads can be in the range of 1-12 kips. These side loads can affect aspects of the universal test system such as wedge deflection and bending, bearing joint rotation, grip alignment, and load cell errors due to friction. According to various embodiments, the wedge assembly can be designed to offset some of these aspects.

In the present embodiment, wedge 313 is slidably attached to adjacent guide block 307 with retainer clip 403, as described in more detail above with regard to FIG. 4. In addition, wedge 313 is slidably attached to actuator interface 309 via base clip 401. Guide blocks 307 can be attached to test frame adapter 311 in some examples. As shown, the wedge assembly has been pushed upwards by an actuator rod such that the wedge 313 and positioning block 801 have closed together around the coupon 805. The upper and lower grip assemblies have also been moved vertically along the guide rods (not shown) such that both the upper and lower grip assemblies have secured opposite ends of the coupon for testing. Although one particular wedge assembly and grip assembly is shown in the present embodiment, various configurations of wedges, with different dimensions and features can be included based on factors such as the type and size of the coupons to be tested and the type of testing to be performed.

With reference to FIG. 9, shown is one example of a universal grip system holding a coupon with a four-fastener configuration. In the present embodiment, the grip system is shown without linear bearings, guide posts, or link plates. However, both the upper and lower grips are shown holding a coupon 901. The coupon 901 includes four fasteners joining two different samples. These samples can be made of the same or different materials, depending on the test.

In the present embodiment, the upper wedge assembly and lower wedge assembly are similar to one another, so only the lower wedge assembly will be described for simplicity. As shown, the lower wedge assembly includes wedge 313, first positioning block 801, and second positioning block 803. The first positioning block 801 contacts and secures the coupon along a grip interface 807 and slides vertically along an axis parallel to the coupon relative to second positioning block 803 as first positioning block 801 moves in conjunction with actuator interface 309 and wedge 313. The first positioning block 801 can also maintain centerline alignment of the coupon without the need to use shims, in some examples. The second positioning block 803 can be fastened to adjacent guide block 307 and can allow first positioning block 801 to slide up and down vertically against it, while providing lateral support during an application of forces during a materials test. Wedge 313 can contact coupon 901 at the fastener locations and provide anti-rotation support at these locations.

According to various embodiments, the first positioning block 801 can provide lateral support for the coupon 901 along the grip interface 807. Furthermore, the surface of wedge 313 facing coupon 901 can provide a support fixture to coupon 901 in the event of premature failure due to buckling during a compression test. In the present example, wedge 313 does not include a grip interface at its base, although a grip interface can be included in some embodiments. The configuration shown in the present example can be used for bearing tests according to various embodiments. For example, during some tests, bearing side loads can be in the range of 1-12 kips. These side loads can affect aspects of the universal grip system such as wedge deflection and bending, bearing joint rotation, grip alignment, and load cell errors due to friction. According to various embodiments, the wedge assembly can be designed to offset some of these aspects.

In the present embodiment, wedge 313 is slidably attached to adjacent guide block 307 with retainer clip 403, as described in more detail above with regard to FIG. 4. In addition, wedge 313 is slidably attached to actuator interface 309 via base clip 401. Guide blocks 307 can be attached to test frame adapter 311 in some examples. As shown, the wedge assembly has been pushed upwards by an actuator rod such that the wedge 313 and positioning block 801 have closed together around the coupon 901. The upper and lower grip assemblies have also been moved vertically along the guide rods (not shown) such that both the upper and lower grip assemblies have secured opposite ends of the coupon for testing. Although one particular wedge assembly and grip assembly is shown in the present embodiment, various configurations of wedges, with different dimensions and features can be included based on factors such as the type and size of coupons to be tested and the type of testing to be performed.

Operating Examples

Figure 10:
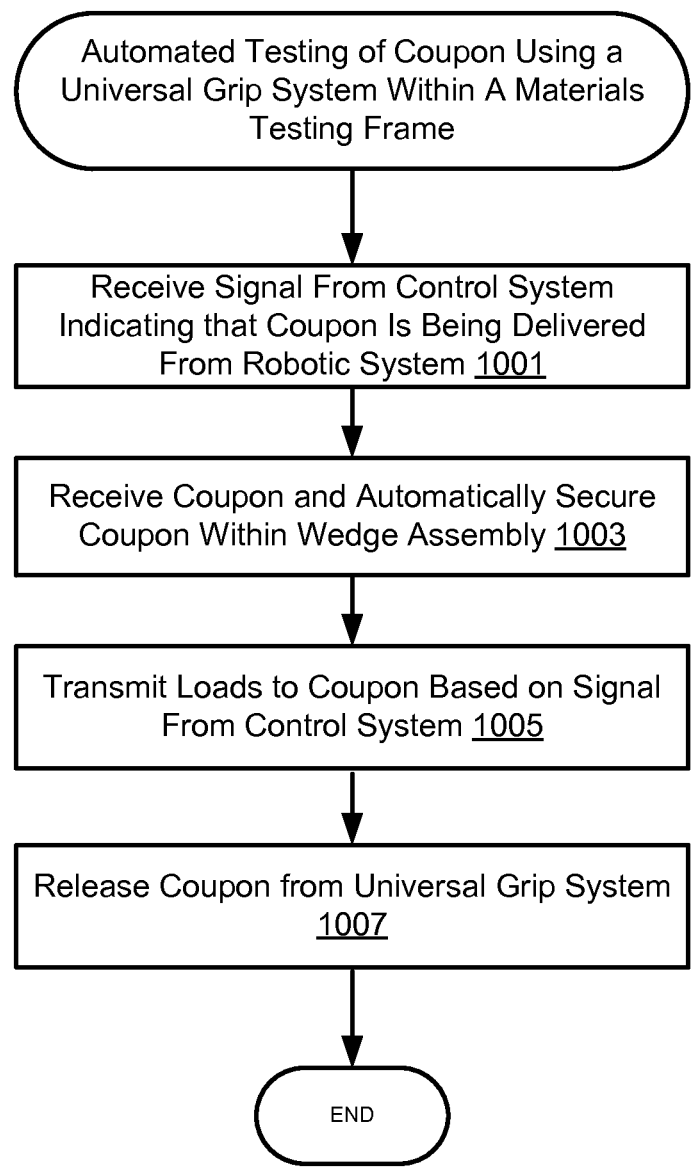
FIG. 10 is a process flowchart for automated testing of a coupon using a universal grip system within a material test frame, in accordance with some embodiments.

As described with regard to the above figures, using a universal grip system can improve materials testing of coupons within an environmental chamber by allowing mechanization of the process and sequential testing without disturbing the environmental conditions within the chamber between tests. With reference to FIG. 10, shown is a process flowchart for automated testing of a coupon using a universal grip system within a materials testing frame, in accordance with some embodiments. In particular, a signal is received from a control system (such as the one shown in FIG. 1), indicating that a coupon is being delivered from a robotic system to the universal grip system at 1001. As shown in FIG. 1, a robotic arm can transport a coupon to the universal grip system in some examples. Next, the universal grip system receives the coupon and automatically secures the coupon within the wedge assembly at 1003. As described in more detail above with regard to various figures, including FIG. 5, an actuator included as part of the test frame can be used to push the wedge within the universal grip system to secure and hold the coupon.

In the present embodiment, once the coupon is secured, loads are transmitted to the coupon at 1005 based on a signal from the control system. As described in more detail above with regard to various figures, the types of loads can include tension, compression, and/or bearing tests, depending on the types of testing to be performed and the types of coupons to be tested. Once testing is complete, the coupon can be released from the universal grip system at 1007. In some examples, the coupon can be retrieved by a robotic arm that transports the coupon to a trash collection area. This robotic arm can be the same arm that is used to load coupons into the universal grip system in some examples. In other examples, two separate robotic arms can be used: one to deliver coupons to the universal grip system and another to retrieve post-test coupons from the universal grip system. Once the coupon is released from the universal grip system, the process can begin again if more coupons are to be tested.

The process described in the present embodiment can be performed within an environmental chamber without the need to open the chamber or disturb the environmental conditions inside. Accordingly, this process can be repeated to sequentially test a batch of coupons within the test frame. Furthermore, this process can improve the throughput of materials testing and provide more time and cost effective testing than previous manually loaded systems.

Examples of Aircraft

Figure 11A:
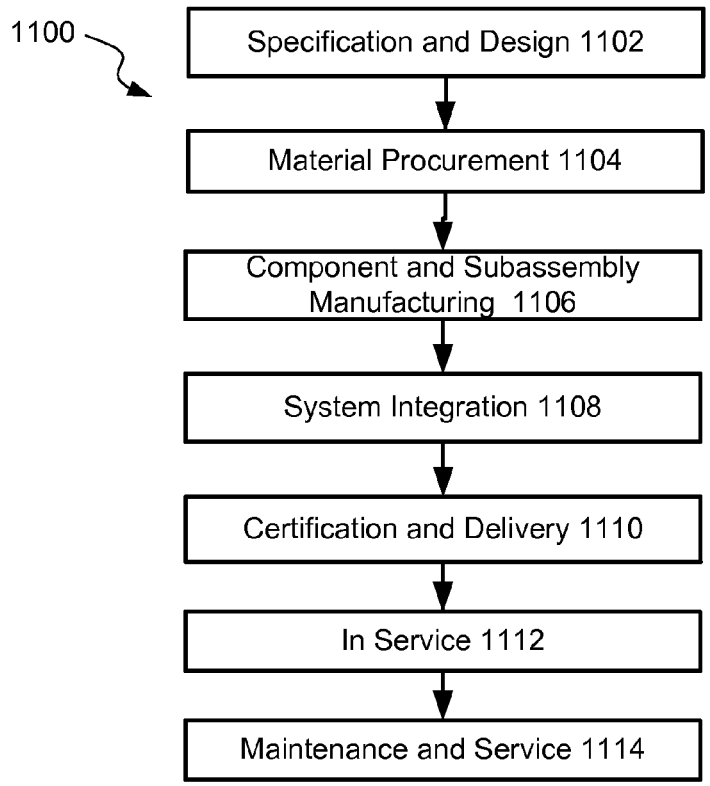
FIG. 11A is a process flowchart reflecting key operations in the life cycle of an aircraft from early stages of manufacturing to entering service, in accordance with some embodiments.

An aircraft manufacturing and service method 1100 shown in FIG. 11A and an aircraft 1130 shown in FIG. 11B will now be described to better illustrate various features of processes and systems presented herein. During pre-production, aircraft manufacturing and service method 1100 may include specification and design 1102 of aircraft 1130 and material procurement 1104. The production phase involves component and subassembly manufacturing 1106 and system integration 1108 of aircraft 1130. Thereafter, aircraft 1130 may go through certification and delivery 1110 in order to be placed in service 1112. While in service by a customer, aircraft 1130 is scheduled for routine maintenance and service 1114 (which may also include modification, reconfiguration, refurbishment, and so on). While the embodiments described herein relate generally to pre-production of commercial aircraft, they may be practiced at other stages of the aircraft manufacturing and service method 1100.

Each of the processes of aircraft manufacturing and service method 1100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of vendors, subcontractors, and suppliers; and an operator may be an airline, leasing company, military entity, service organization, and so on.

Figure 11B:
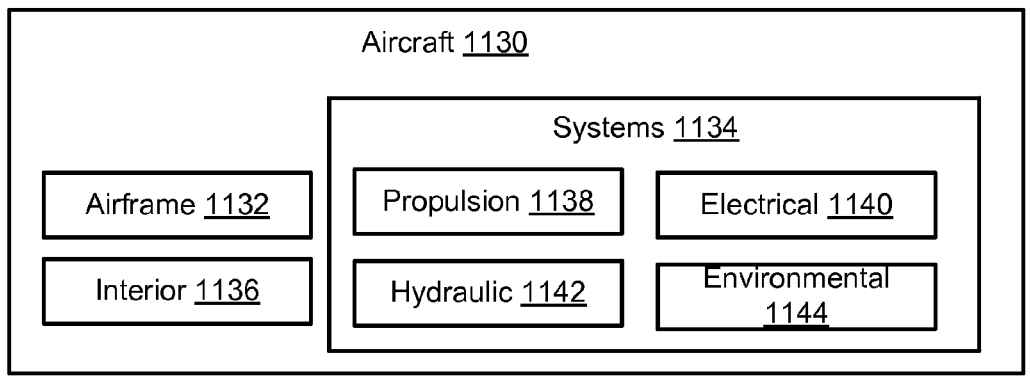
FIG. 11B is a block diagram illustrating various key components of an aircraft, in accordance with some embodiments.

As shown in FIG. 11B, aircraft 1130 produced by aircraft manufacturing and service method 1100 may include airframe 1132, interior 1136, and multiple systems 1134. Examples of systems 1134 include one or more of propulsion system 1138, electrical system 1140, hydraulic system 1142, and environmental system 1144. Any number of other systems may be included in this example. Although an aircraft example is shown, the principles of the disclosure may be applied to other industries, such as the automotive industry.

Apparatus and methods embodied herein may be employed during any one or more of the stages of aircraft manufacturing and service method 1100. For example, without limitation, components or subassemblies corresponding to component and subassembly manufacturing 1106 may be fabricated or manufactured in a manner similar to components or subassemblies produced while aircraft 1130 is in service.

Also, one or more apparatus embodiments, method embodiments, or a combination thereof may be utilized during component and subassembly manufacturing 1106 and system integration 1108, for example, without limitation, by substantially expediting assembly of or reducing the cost of aircraft 1130. Similarly, one or more of apparatus embodiments, method embodiments, or a combination thereof may be utilized while aircraft 1130 is in service, for example, without limitation, maintenance and service 1114 may be used during system integration 1108 to determine whether parts may be connected and/or mated to each other.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A universal grip system comprising:
   a grip assembly comprising:
      a first wedge slidably supported in the grip assembly; and
      a second wedge slidably supported in the grip assembly,
      wherein the first wedge and the second wedge include:
         a base portion and a tip portion;
         a grip zone at the tip portion for gripping a coupon between the interior surfaces of the first wedge and the second wedge during testing, and
         a support zone adjacent to the grip zone for preventing buckling and rotation of the coupon during testing, the support zone extending from the tip portion and away from the base portion of each of the first wedge and the second wedge;
         wherein the spacing between the interior surfaces of the first wedge and the second wedge is wider at the support zone than at the grip zone; and
         wherein the spacing between the interior surfaces of the first wedge and the second wedge is uniform within the support zone and within the grip zone;
   a first guide post; and
   a second guide post,
      wherein the grip assembly is slidably coupled to the first guide post and the second guide post such that the grip assembly is movable in a sliding direction.

2. The universal grip system of claim 1, wherein the first wedge is movable with the first grip in a second sliding direction not parallel to the first sliding direction.

3. The universal grip system of claim 2, wherein the first grip further comprising a third wedge slidably supported in the first grip, and wherein the third wedge is movable with the first grip in a third sliding direction not parallel to the first sliding direction.

4. The universal grip system of claim 3, further comprising a base clip engaging the first wedge and the third wedge and allowing the first wedge and the third wedge to move with respect to each other in a direction normal to the first sliding direction.

5. The universal grip system of claim 3, further comprising a link plate, wherein the link plate aligns the first wedge and the third wedge relative to each other within a plane parallel to the first sliding direction.

6. The universal grip system of claim 5, wherein the link plate is removable.

7. The universal grip system of claim 3, further comprising an actuator interface having a surface engaging the first wedge and the third wedge.

8. The universal grip system of claim 1, wherein the first grip further comprises a first guide block, the first guide block slidably supporting the first wedge.

9. The universal grip system of claim 8, wherein the first grip further comprises a second guide block, the second guide block slidably supporting an additional wedge or fixedly supporting a positioning block.

10. The universal grip system of claim 8, wherein the first grip further comprises a retainer clip engaging the first guide block and first wedge allowing the first wedge to slide relative to the first guide block.

11. The universal grip system of claim 1, wherein the first grip comprises a thermally neutral material, and wherein the second grip comprises the thermally neutral material.

12. The universal grip system of claim 1,
    wherein the first grip is thermally insulated from the first guide post and second guide post, and
    wherein the second grip is thermally insulated from the first guide post and second guide post.

13. The universal grip system of claim 12, wherein the first grip and the second grip are thermally insulated from the first guide post and the second guide post by ceramic spacers.

14. The universal grip system of claim 13, wherein the first grip is slidably coupled to the first guide post using a first linear bearing, and wherein one of the ceramic spacers is disposed between the first linear bearing and the first grip.

15. The universal grip system of claim 1, wherein the first wedge and the second wedge are made from a material having a coefficient of thermal expansion less than $6 \times 10^{-6}$ inch/inch ° F.

16. The universal grip system of claim 1, wherein the first wedge and the second wedge are made from a nickel-iron alloy.

17. A method for testing of a coupon, the method comprising:
    securing the coupon using a universal grip system comprising a grip assembly, the grip assembly comprising a first wedge slidably supported in the grip assembly and a second wedge slidably supported in the grip assembly,
        wherein securing the coupon comprising sliding the first wedge and the second wedge in the grip assembly to engage the coupon with the first wedge and the second wedge;
        wherein the first wedge and the second wedge include:
            a base portion and a tip portion
            a grip zone at the tip portion for gripping a coupon between the interior surfaces of the first wedge and the second wedge during testing, and
            a support zone adjacent to the grip zone for preventing buckling and rotation of the coupon during testing, the support zone extending from the tip portion and away from the base portion of each of the first wedge and the second wedge;
            wherein the spacing between the interior surfaces of the first wedge and the second wedge is wider at the support zone than at the grip zone; and
            wherein the spacing between the interior surfaces of the first wedge and the second wedge is uniform within the support zone and within the grip zone;
    transmitting a load to the coupon based on a signal from a control system; and
    releasing the coupon from the universal grip system,
        wherein releasing the coupon comprising sliding the first wedge away from the second wedge in the grip assembly and disengaging the coupon from the first wedge and the second wedge.

18. The method of claim 17, wherein the first grip and the second grip are each supported by a first guide post and a second guide post as the first grip moves relative to the second grip during securing the coupon, transmitting the load, and releasing the coupon.

19. The method of claim 18, wherein the first grip and the second grip are each thermally insulated from the first guide post and the second guide post.

* * * * *